US007879115B2

(12) United States Patent
Garetz et al.

(10) Patent No.: US 7,879,115 B2
(45) Date of Patent: Feb. 1, 2011

(54) METHOD FOR USING A STATIC ELECTRIC FIELD TO INDUCE CRYSTALLIZATION AND TO CONTROL CRYSTAL FORM

(75) Inventors: Bruce A. Garetz, New York, NY (US); Allan S. Myerson, Chicago, IL (US); Stephen Arnold, New York, NY (US); Janice E. Aber, Great Neck, NY (US)

(73) Assignee: Intellectual Ventures Holding 19, LLC, Las Vegas, NV (US)

( * ) Notice: Subject to any disclaimer, the term of this patent is extended or adjusted under 35 U.S.C. 154(b) by 48 days.

(21) Appl. No.: 11/104,714

(22) Filed: Apr. 13, 2005

(65) Prior Publication Data

US 2005/0256300 A1 Nov. 17, 2005

Related U.S. Application Data

(60) Provisional application No. 60/561,583, filed on Apr. 13, 2004.

(51) Int. Cl.
*B01D 9/02* (2006.01)
(52) U.S. Cl. .................................. 23/295 R; 23/296
(58) Field of Classification Search .............. 536/124; 127/61; 530/418, 427; 23/295; 204/157.15, 204/157.68, 157.9
See application file for complete search history.

(56) References Cited

U.S. PATENT DOCUMENTS

| 5,597,457 | A | * | 1/1997 | Craig et al. ................. 204/165 |
| 6,426,406 | B1 | * | 7/2002 | Myerson et al. ............. 530/418 |
| 7,193,084 | B2 | * | 3/2007 | Werling et al. .............. 544/366 |

OTHER PUBLICATIONS

Doerr et al., "Widening the protein crystallization bottleneck" Nature Methods (2006) vol. 3 No. 12, p. 961.*
Thakur et al., "Improved Success of Sparse Matrix Protein Crystallization Screening with Heterogeneous Nucleating Agents" PLoS One (2007) issue 10, e1091, pp. 1-6.*
Jain et al., "Polymorphism in Pharmacy" Indian Drugs (1986) vol. 23 No. 6, pp. 315-329.*
Vippagunta et al., "Crystalline Solids" Advanced Drug Delivery Reviews (2001) vol. 48 pp. 3-26.*
Mezhidov et al., "Mechanism of Appearance of Crystallization Centers on the surface of supersaturated solutions under the action of an electric field" Zhurnal Fizichekoskoi Khimii (1974) vol. 48 No. 9, pp. 2357-2358.*
Certified English translation of Mezhidov et al. above, Zhurnal Fizichekoskoi Khimii (1974) vol. 48 No. 9, pp. 2357-2358.*
"Ammonium Chloride" downloaded from Drugs.com, pp. 1-4, last revised Aug. 2006.*
Sazaki et al., "Novel coupling effects of the magnetic and electric fields on protein crystallization" Journal of Crystal Growth (2004) vol. 262 pp. 499-502.*
Saban et al., "Thermodynamics of Crystal Nucleation in an External Electric Field" Cryst. Res. Technol. (2002) vol. 37 pp. 1188-1199.*
Taleb et al., "Crystallization of proteins under an external electric field" Journal of Crystal Growth (1999) vol. 200 pp. 575-582.*
Iwai et al., "Effect of a Direct-Current Electric Field on the Separation of Binary Systems Containing Organic Compounds Using Crystallization" Ind. Eng. Chem. Res. (2003) vol. 42 pp. 6638-6640.*
Huang et al., "Nuclear, Molecular Clustering, and Polymorphic Selectivity: Do Glycine Dimers Exist in Supersaturated Soluations?" University of Wisconsin-Madison, downloaded 2009, 1 page.
Pornachary et al., "Effects of Impurities on Crystallisation," Feb. 2007, 1 page.
Chew et al., "Control of Batch Cooling Crystallization of Glycine," downloaded 2009, 7 pages.
Gnanasambandam et al., "Force Field for Molecular Dynamics Studies of Glycine/Water Mixtures in Crystal/Solution Environments," J. Phys. Chem. B 2009, 113, 752-758.
Reply Pursuant to 37 C.F.R. § 1.116, United States Patent and Trademark Office, Bruce A. Garetz et al., U.S. Appl. No. 11/104,714, filed Apr. 13, 2005, pp. 1-8.
Chew et al., "Control of Batch Cooling Crystallization of Glycine," Poster Session: Pharmaceutical Technology, The Preliminary Program for 2005 Annual Meeting (Cincinnati, OH)http://aiche.confex.com/aiche/2005/preliminaryprogram/abstract_4655.htm, downloaded Apr. 14, 2009, 1 page.

* cited by examiner

*Primary Examiner*—Eric S Olson
(74) *Attorney, Agent, or Firm*—Woodcock Washburn LLP (57) ABSTRACT

Applying a strong static DC electric field to supersaturated aqueous glycine solutions resulted in the nucleation of the γ polymorph attributed to the electric-field induced orientation of the highly polar glycine molecules in large preexisting solute clusters, helping them organize into a crystalline structure. A method to induce crystallization and to prepare polymorphs and/or morphologies of materials by using a static electric field to cause nucleation and crystal growth to occur in a supersaturated solution in such a way as to obtain a crystal structure that would not normally appear without the use of the static electric field. Aqueous glycine solutions were prepared by combining solid glycine and water. Supersaturated solutions were generated by heating the tubes to 62-64° C. and holding them at that temperature in an ultrasonicator overnight. Once the glycine was completely dissolved, the solutions were slowly cooled to room temperature. A chamber was constructed consisting of two brass electrodes separated by a 5 mm insulating gap, with a hole drilled down through the center, parallel to the gap-electrode interface, with a diameter large enough to accommodate the test tube. A DC voltage was applied across the electrodes, large enough to produce electric fields in the range of 400,000 to 800,000 V/m. Tests tubes containing the aged solutions were placed in the high-voltage chamber. Exposure of the aged solutions to fields of 600,000 V/m resulted in crystallization typically within 30-90 min. The onset of nucleation was observed visually by the formation of a needle-shaped crystallite.

14 Claims, 3 Drawing Sheets

METHOD FOR USING A STATIC ELECTRIC FIELD TO INDUCE CRYSTALLIZATION AND TO CONTROL CRYSTAL FORM

STATEMENT OF RELATED APPLICATIONS

This patent application is based on and claims priority on U.S. Provisional Patent Application No. 60/561,583 having a filing date of 13 Apr. 2004, currently pending.

BACKGROUND OF THE INVENTION

1. Field of the Invention

This invention relates generally to the field of inducing nucleation in supersaturated solutions and specifically to the novel process of inducing nucleation in supersaturated solutions using a static electric field to, among other things, to create polymorphs that are unexpected and/or unknown.

2. Prior Art

Crystallization from liquid solution is a ubiquitous phase transition that has great technological importance, but whose mechanism is not well elucidated. It is used to separate and purify industrially important substances such as pharmaceuticals, pigments, dyes and explosives. Nucleation, the initial step in the process of crystallization involving the formation of a critical nucleus, is still poorly understood. There is growing evidence that nucleation from solution is often a two-step process: the formation of a nanoscale, liquid-like solute cluster, followed by an organizational step in which the cluster takes on a crystalline structure.

The process of nucleation is further complicated when the solute under study has the possibility of crystallizing into more than one crystal structure, known as polymorphism. Different polymorphs of a substance may exhibit great differences in chemical and physical properties such as melting point, solubility, dissolution rate, bioavailability and hardness. Living organisms are able to control morphology and polymorphism through biomineralization. The addition of certain impurity chemicals can inhibit or promote the growth of particular crystal surfaces. Such tailor-made additives operate through stereospecific interactions not unlike enzyme-substrate interactions. New polymorphs of organic molecules constitute novel materials that may have important industrial applications. The crystal structure of a material determined by x-ray diffraction gives a complete picture of the arrangement of the atoms (or molecules) of the chemical species in the crystalline state.

The term "polymorphism" is contrasted with "morphology." Crystals are solids with the atoms, molecules, or ions in a regular repeating structure. The overall external form is referred to as crystal morphology. The term morphology refers to the external shape of the crystal and the planes present, without reference to the internal structure. Crystals obtained experimentally can display different morphology based on different conditions, such as, for example, growth rate, stirring, and the presence of impurities. In contrast, polymorphism refers to the internal alignment and orientation of the molecules. A substance can have several distinct polymorphs and only one morphology, or several distinct morphologies for only one polymorph. Just because the morphology changes does not mean there is a new polymorph, and vice versa. Unlike with different morphologies, one cannot tell by visual observation whether one has a different polymorph.

The prior art produces a substance with a known morphology and crystal structure. It does not produce a substance of unknown crystal structure (a new polymorph) or of unexpected structure (a known polymorph that would not normally occur under these conditions). As discussed above, there is an important distinction between morphology and polymorphism. Morphology is the external appearance of the crystal. In contrast, polymorphism refers to the internal structure of the crystal. It is important to note that crystals of a given substance with different morphologies have the same physical properties (such as melting point, solubility, electrical conductivity, etc) while different polymorphs of the same substance have different properties (e.g., diamond and graphite, which are different polymorphs of carbon).

Polymorphism is quite common in the elements and in inorganic and organic compounds and results in property changes. A dramatic example is carbon, which can crystallize as graphite or as diamond. Diamond is a cubic crystal, whereas graphite is hexagonal. In addition, properties such as hardness, density, shape, vapor pressure, dissolution rate, and electrical conductivity are all quite different for these two solids. These major differences in the properties of two polymorphs are not unique to carbon and can occur in all materials that display polymorphism. Many of the early identifications of polymorphs were minerals, such as calcium carbonate, which has three polymorphs (calcite, aragonite, and vaterite) and zinc sulfide, which has three polymorphs (wurtzite, sphalerite, and matraite). Some well known species have large numbers of polymorphs, for example water, which has eight different solid forms of ice. Organic molecular crystals often have multiple polymorphs that can be of great significance in the pharmaceutical, dye and explosives industries.

Under a given set of conditions, one polymorph is the thermodynamically stable form. This does not mean, however, that other polymorphs cannot exist or form at these conditions, only that one polymorph is stable and other polymorphs present can transform to the stable form. An example of this can be seen in heating (or cooling) a crystalline material with multiple polymorphs. As the temperature changes, the material will eventually enter a region where another polymorph is the stable form. The transformation of one polymorph to another, however, will occur at some rate that may be rapid or very slow. The transformation rate varies because the rate of transition of polymorphs depends on the type of structural changes that are involved.

Transformations can be categorized by the types of structural changes involved, which can roughly be related to the rate of transformation. For example, a transformation in which the lattice network is bent but not broken can be rapid. This type of transformation is known as displacive transformation of secondary coordination. Another type of rapid transformation can involve the breakage of weaker bonds in the crystal structure with the stronger bonds remaining in place. This is then followed by the rotation of parts of the molecule about the structure and the formation of new bonds. This type of transformation is a rotational disorder transformation. Slow transformations usually involve the breakage of the lattice network and major changes in the structure or type of bonding.

Polymorphic transformations also can be classified as first- or second-order transitions. In a first-order transition, the free energies of the two forms become equal at a definite transition temperature, and the physical properties of the crystal undergo significant changes upon transition. In a second-order transition, there is a relatively small change in the crystal lattice, and the two polymorphic forms will be similar. There is no abrupt transition point in a second order transition, although the heat capacity rises to a maximum at a second order transition point.

When a material is crystallized from solution, the transition between polymorphs can occur at a much higher rate because the transition is mediated by the solution phase. Polymorphs of a given material will have different solubilities at a given temperature, with the more stable material having a lower solubility (and a higher melting point) than the less stable polymorph. If two polymorphs are in a saturated solution, the less stable polymorph will dissolve and the more stable polymorph will grow until the transition is complete. The rate of the transition is a function of the difference in the solubility of the two forms and the overall degree of solubility of the compounds in solution. This transition requires that some amount of the stable polymorph be present, meaning that the stable polymorph must nucleate at least one crystal for the transition to begin. If a slurry of solution and crystals of a polymorph stable at a high temperature is cooled to a lower temperature, where another polymorph is the stable phase, the transition of the crystals already present will depend on the presence of nuclei of the new stable phase. The more of these nuclei present, the faster the transition will occur.

It is often possible to crystallize a metastable polymorph by applying a large supersaturation (for example rapid cooling) so that crystals of the metastable form appear before crystals of the stable form. When this occurs, if the solid is removed from the solution rapidly and dried, it is possible to obtain samples of a metastable polymorph that will not easily transform to the stable phase unless heated. If the crystals of the metastable polymorph are left in solution for any length of time, they will likely transform to the stable form by going through the solution phase. If seeds of the stable polymorph are added to the solution, the transition will occur more rapidly. At first-order phase-transition temperatures, the solubility of the two forms will be equal and both can exist.

When a material that displays polymorphism is crystallized, a metastable phase often appears first and then transforms into a stable form. This observation is summarized by Ostwald's step rule, which is also known as the Law of Successive Reactions. This law states that, in any process, the state that is initially obtained is not the most stable state but the least stable state that is closest, in terms of free-energy change, to the original state. In a crystallization process, therefore, it is possible to envision the phase transformation first occurring into the least stable polymorph (or even an amorphous phase), which transforms through a series of stages to successively more stable forms until the equilibrium form is obtained. While Ostwald's law has been observed in a wide variety of systems, it is most likely to be seen in organic molecular crystals.

Another interesting feature of organic molecular crystals is that the molecular conformation of a species can be different in two polymorphs of the same material. By molecular conformation, we are referring to the shape of the molecule. The same molecule can display different shapes (conformations by rotations about single bonds for example. Conformational polymorphism is the existence of polymorphs of the same substance in which the molecules present are in different conformations.

It is known that by subjecting some supersaturated solutions to laser light, the onset of nucleation occurs. Prior to nucleation, the supersaturated solution contains "clusters" of molecules that are not arranged in the lattice structure of a crystal. The oscillating optical electric field of the laser light helps to align or organize the molecules in the clusters, through the optical Kerr effect, into a lattice arrangement resulting in the formation of nuclei and, after time, crystals. Garetz, B. A. et al., Nonphotochemical, Polarization-Dependent, Laser-Induced Nucleation in Supersaturated Aqueous Urea Solutions, Physical Review Letters, Vol. 77, No. 16, pp. 3475-6 (1996). In this study, we accidentally discovered that intense nanosecond near-infrared laser pulses could induce supersaturated aqueous urea solutions to nucleate. We called this phenomenon non-photochemical laser-induced nucleation (NPLIN) to distinguish it from the better-known, century-old field of ultraviolet and visible light-induced nucleation in supersaturated vapors, the mechanism of which typically involves the photochemical generation of a nonvolatile product that acts as a nucleus for the growth of the condensed phase.

We also have shown that supersaturated aqueous glycine 4.5 to 4.8 molal (3.7 to 3.9 M) could be induced to crystallize into either the α or γ polymorph depending on the polarization state of the laser beam. Garetz, B. A. et al., Physical Review Letters, Vol. 89, No. 14, pp. 175501 (2002). Spontaneous nucleation at these concentrations always produces α glycine, although γ glycine is the most stable polymorph. We attributed both the urea and glycine observations to the interaction of preexisting large solute clusters with the intense electric field of the light, causing an organization of the cluster through the electric field-induced alignment of molecules (i.e. the optical Kerr effect) in the cluster. Linear and circular polarizations induce different types of alignment and thus induce the nucleation of different polymorphs. This "polarization switching" is the strongest evidence to date that the mechanism for NPLIN is not photochemical.

The present invention concerns the novel application of a static (DC) electric field to a supersaturated solution, rather than the application of an oscillating optical electric field that was the subject of the Garetz, et al. paper discussed above and the previous laser-related patent by Myerson and Garetz, U.S. Pat. No. 6,426,406, and the unexpected result that a static (DC) electric field will induce nucleation in the supersaturated solution.

BRIEF SUMMARY OF THE INVENTION

Crystallization from solution occurs from a supersaturated solution. Supersaturated solutions are metastable, meaning that they sometimes will not spontaneously crystallize. A given substance can crystallize into more than one crystal structure. This is because the molecules must form a cluster of the critical size that must arrange itself into a crystal lattice. In organic molecular crystals, because of the complexity of the molecules, this often can be difficult. That is, the molecules have trouble forming a nucleus.

Briefly, the present invention is a novel method for inducing nucleation in supersaturated solutions and for creating new or unexpected polymorphs and morphologies of known substances. The novel polymorphs created with the present method have internal crystal structures that are different than those currently known (the new polymorphs) or different than what would be expected by one of ordinary skill in the art without use of the present method (the unexpected polymorphs). Surprisingly, the new or unexpected polymorphs can be created without chemically affecting or influencing the solution (that is, changing the chemistry of the solution). In effect, the present method is a non-chemical method of affecting the solution in a manner different than the prior art.

Aqueous glycine solutions were prepared by combining solid glycine and water. Supersaturated solutions were generated by heating the tubes to 62-64° C. and holding them at that temperature in an ultrasonicator overnight. Once the glycine was completely dissolved, the solutions were slowly cooled to room temperature. A chamber was constructed consisting of two brass electrodes separated by a 5 mm insulating gap, with a hole drilled down through the center, parallel to the gap-electrode interface, with a diameter large enough to accommodate the test tube. A DC voltage was applied across the electrodes, large enough to produce electric fields in the range of 400,000 to 800,000 V/m. Tests tubes containing the aged solutions were placed in the high-voltage chamber. Exposure of the aged solutions to fields of 400,000 V/m was not sufficient to induce nucleation. When the electric field strength was increased to 600,000 V/m crystallization was typically observed within 30-90 min. The onset of nucleation was observed visually by the formation of a needle-shaped crystallite. It is thus disclosed here for the first time that intense static electric fields can induce nucleation in supersaturated solutions.

The internal structure of a crystal is referred to as polymorphism for substances and allotropism for elements. Polymorphic crystals are chemically identical but have different arrangements of atoms (or molecules) in the crystal lattice giving the solids different properties. Crystals of a given substance with different polymorphs have chemical and physical properties that vary. The fact that the solid properties can change makes different polymorphs behave differently when used for applications. For examples, a different polymorph of a dye would give a different color, and different polymorphs of drugs can have different bioavailability and dissolution properties. Much effort is spent in trying to find if a particular substance has additional polymorphs and in trying to prepare a particular polymorph.

This invention makes use of high-intensity static direct current (DC) electric fields to induce nucleation in a supersaturated solution and to induce the nucleation of polymorphs, including unknown and/or unexpected polymorphs. By subjecting supersaturated solutions to a static electric field, the onset of nucleation occurs. Depending on the system, macroscopic crystals form on a timescale of minutes (aqueous L-alanine) to hours (aqueous glycine). The interaction involves responses of molecules to the applied static electric field, known as the DC Kerr effect (the DC-field-induced orientation of molecules) or electrostriction (the DC-field-induced movement of molecules into regions of high electric field). This interaction is different than the one involved in the laser-induced crystallization that was the subject of U.S. Pat. No. 6,426,406 to Myerson and Garetz. In that case, the light polarizes a molecule, meaning that it applies forces to the electrons and nuclei that comprise the molecule, and induces transient changes in the charge distribution in the molecule through the optical (AC) Kerr effect. In the present invention, the static electric field interacts with the permanent electric dipole moment of the molecule, causing it to orient so that the molecular dipole is parallel to the applied electric field, through the DC Kerr effect. The unexpected discovery disclosed herein is that by using this technique, a supersaturated solution can be induced to nucleate, and a polymorph can be created of an unknown morphology or polymorphism or of a morphology or polymorphism that is unexpected under given conditions. The electric-field-induced changes in molecular orientation distribution can temporarily change the interactions between the molecules in a cluster, thereby changing the rate of formation of different polymorphs.

The present invention is a method of using an intense static electric field to cause the nucleation and crystal growth to occur, and in some cases in such a way as to obtain a crystal morphology or polymorphism that is unknown and/or unexpected under given conditions by the person of ordinary skill in the art. Under a defined set of conditions, specific polymorphs will be present in the solution and will be known and expected by the person of ordinary skill in the art. More specifically, a variation in the defined conditions can change the expected and known polymorph. The present method can be used to prepare new polymorphs of material that would not ordinary be observed to occur or prepare polymorphs that are not expected by the person of ordinary skill in the art to occur under given conditions in the absence of the method.

Applying a strong static electric field to supersaturated aqueous glycine solutions resulted in the nucleation of the γ polymorph. This is the first report of a strong DC field inducing the nucleation of a neutral solute in a supersaturated solution. We attribute this effect to the electric-field induced orientation of the highly polar glycine molecules in large preexisting solute clusters, helping them organize into a crystalline structure. This result also lends further support to our proposed optical-Kerr mechanism for non-photochemical laser-induced nucleation.

An object of this invention generally is the use of a static electric field to induce the nucleation of a polymorph or morphology from a supersaturated solution that is different from the polymorph or morphology that would spontaneously nucleate from the supersaturated solution under the same general conditions, but in the absence of the static electric field.

Another object of this invention is the use of a static electric field at various field strengths and exposure times to induce the nucleation of a polymorph or morphology from a supersaturated solution that is different from the polymorph or morphology that would spontaneously nucleate from the supersaturated solution under the same general conditions, but in the absence of the static electric field.

Another object of this invention is the use of various different process conditions (i.e., at various temperatures depending on the solubility of the compound being subjected to the static electric field; various aging times; various supersaturation levels; various methods of achieving supersaturation such as cooling, heating, solvent evaporation, and changing solvent composition; and various different solvents such as organic or inorganic solvents) to induce the nucleation of a polymorph or morphology from a supersaturated solution that is different from the polymorph or morphology that would spontaneously nucleate from the supersaturated solution under the same general conditions, but in the absence of the static electric field.

Another object of this invention is to provide of method of inducing an unknown and/or unexpected polymorph or morphology by spontaneous nucleation in a solution under a set of conditions through the use of a static electric field without changing the chemistry of the solution.

These objects, and other objects, features and advantages of the invention will become apparent to those of ordinary skill in the art when the following detailed description of the preferred embodiments is read.

DETAILED DESCRIPTION OF A PREFERRED EMBODIMENT

1. Introduction

We have proposed a mechanism for NPLIN that involves the optical electric field induced alignment of solute molecules in a preexisting solute cluster, helping the cluster organize into a crystal. One issue with this hypothesis is that the calculated induced-dipole interaction energy in our NPLIN experiments ½ $(\Delta\alpha)E^2=10^{-4}$ kT is orders of magnitude too small to account for the observed reduction in nucleation time, where E is the oscillating optical electric field ($6\times10^7$ V/m), $\Delta\alpha$ is the solute molecule polarizability anisotropy, k is the Boltzmann constant and T is the Kelvin temperature. Cooperative effects among many solute molecules in a large solute cluster might account for this discrepancy.

There is theoretical evidence that a strong DC electric field can induce crystallization. Molecular dynamics simulations by Svishchev et al. showed that supercooled water can be induced to crystallize by a DC field of magnitude $5\times10^9$ V/m. Svishchev, I. M. et al., Physical Review Letters, Vol. 73, pp. 975-978 (1994). Simulations of supercooled water in the absence of a field have yielded crystallization only once, after a seven-year effort by Matsumoto et al. Matsumoto, M. et al., Nature, Vol. 416, pp. 409-413 (2002). DC electric fields have been used by a number of researchers to affect the crystallization of proteins and ionic compounds from solution, although the mechanism here typically involves the migration of charged protein molecules or ions, thus altering the local supersaturation or causing convection. Nanev, C. N. et al., Journal of Crystal Growth, Vol. 232, pp. 285-293 (2001); Taleb, M. et al., Journal of Crystal Growth, Vol. 200, pp. 575-582 (1999); Penkova, A. et al., Enhancement and Suppression of Protein Crystal Nucleation due to Electrically Driven Convection, Journal of Crystal Growth, in press.

If our proposed mechanism for NPLIN is correct, and the induced-dipole interaction energy $½(\Delta\alpha)E^2=10^{-4}$ kT is sufficient to induce nucleation, then perhaps a comparable permanent-dipole interaction $\mu E_{DC}=10^{-4}$ kT ought to be sufficient to induce nucleation with a static electric field $E_{DC}$, where p is the permanent dipole moment. Glycine, which is a zwitterion ($^+NH_3CH_2COO^-$) in aqueous solution, has an enormous permanent electric dipole moment, $\mu=47\times10^{-30}$ C m, eight times larger than $\mu_{water}$. The DC electric field that must be applied to produce an interaction energy of $10^{-4}$ kT is $E_{DC}=6\times10^5$ V/m, after accounting for dielectric constant of water. To test this hypothesis, we exposed supersaturated aqueous glycine solutions to strong DC electric fields.

Nucleation in liquid solutions is a complex problem involving two components, and there appear to have been no other reports of static electric field induced nucleation of neutral solutes from supersaturated solutions other than reported here by the present inventors. Nevertheless, this problem is of great theoretical and commercial importance, such as in industrial crystallization processes. The use of such a process to cause nucleation and crystal growth in such a way as to obtain a crystal structure that would not normally form can be used to prepare new polymorphs and morphologies of materials that have not been observed or to obtain a known polymorph under different conditions than those under which the polymorph is usually made.

The present invention is a novel method for inducing nucleation in supersaturated solutions and for creating new or unexpected polymorphs or morphologies of known substances. The novel polymorphs created with the present method have internal crystal structures that are different than those currently known (the new polymorphs) or different than what would be expected by one of ordinary skill in the art without use of the present method (the unexpected polymorphs). Surprisingly, the new or unexpected polymorphs can be created without chemically affecting or influencing the solution (that is, changing the chemistry of the solution). In effect, the present method is a non-chemical method of affecting the solution in a manner different than the prior art.

Glycine is known to form at least three different polymorphs under different conditions. The one that normally forms from neutral aqueous solution is called the alpha form. Another form, known as the gamma form, forms from acidic or basic aqueous solutions. X-ray powder diffraction analysis of the crystals produced upon exposure to an intense static electric field confirmed that the gamma polymorph of glycine was formed. This is a different polymorph than the alpha polymorph that is formed when aqueous glycine nucleates spontaneously. The needle-shaped crystals formed represent a different morphology of gamma glycine than those formed by laser-induced nucleation.

It is thus disclosed here for the first time that a static electric field can induce solutions to crystallize into a polymorph and morphology not normally known and/or expected by the person of ordinary skill in the art. This effect can be extrapolated to compounds other than glycine, L-alanine and urea as these compounds are commonly used by those skilled in the art as base stepping stone compounds, and allows the preparation of new polymorphs or morphologies of materials that have not been observed, or of known polymorphs or morphologies under conditions different than those in which they are usually made.

A static electric field can induce nucleation in supersaturated solutions. In some cases, the crystallites that are formed have a different structure than crystallites that form when the same solution spontaneously nucleates. Such is the case with aqueous glycine solutions with supersaturations $c/c_{sat}$, in the range of 1.8 to 1.9, in which c is the concentration of the solution and $c_{sat}$ is the concentration of a saturated solution. At 25° C., the solubility of glycine, $c_{sat}$, is 22.5 g/100 g.

2. General Methodology

Aqueous glycine solutions were prepared by combining solid glycine and water in 1.3-cm diameter Pyrex test tubes with screw-on caps. Great care was taken to exclude dust from samples. Supersaturated solutions were generated by heating the tubes to 62-64° C. and holding them at that temperature in an ultrasonicator overnight. Once the glycine was completely dissolved, the solutions were slowly cooled to room temperature. Solutions prepared in this way lasted for several weeks before spontaneously nucleating.

Generally, glycine is added to a solvent such as water in an amount and under conditions so as to create a supersaturated solution of glycine in water. It should be noted that this experimental procedure is applicable to solutions other than glycine in water. Those of ordinary skill in the art can produce other supersaturated solutions of compounds in appropriate solvents without undue experimentation.

For example purposes only, suitable compounds include, but are not limited to, pharmaceuticals, amino acids, peptides, proteins, carbohydrates, amines, alkanes, alkenes, alkynes, aromatics, heterocyclic compounds, alcohols, organometallics, carboxylic acids, and derivatives of these compounds. Also for example purposes only, suitable solvents include, but are not limited to, organic, inorganic, and supercritical solvents. Once a compound is selected for subjecting to the electric field, the appropriate solvent is selected. Those of ordinary skill in the art can determine the appropriate solvent for a selected compound without undue experimentation.

A chamber was constructed consisting of two brass electrodes separated by a 5 mm insulating gap, with a hole drilled down through the center, parallel to the gap-electrode interface, with a diameter large enough to accommodate the test tube, to create a high voltage chamber. Test tubes containing the aged solutions were placed in the high voltage chamber.

A DC voltage was applied across the electrodes, large enough to produce electric fields in the range of 400,000 to 800,000 V/m. Tests tubes containing the aged solutions were placed in the high-voltage chamber. It has been found that suitable electric-field exposure times are from approximately 0.1 second to approximately 10 hours. If crystals formed in the test tubes, the crystals were removed from the solution and dried. The structure of these crystals was analyzed by grinding up the crystal into a powder and obtaining an x-ray powder diffraction pattern.

3. Example

Aqueous glycine solutions were prepared in 1.3-cm diameter Pyrex test tubes (1.0-cm inner diameter) with screw-on caps. The reagents, glycine (Plus One Pharmacia Biotech ≧99.7%) and water (Fisher W11-1, Environmental Grade, ≧18 MΩ-cm), were used without further purification. The supersaturated solutions were in the concentration range of 5.5 to 6.0 molal. Glycine was dissolved in water by ultrasonication at 64±1.4° C. over several days, and the resulting solutions were cooled slowly overnight to room temperature, approximately 20° C., where the saturation concentration $c_{sat}$=3.0 molal. These solutions had supersaturations (SS) ranging from 1.85 to 2.0; SS=c/$c_{sat}$, where $c_{sat}$ is the saturation concentration. Such solutions could last from weeks to months before spontaneously nucleating.

Figure 1:
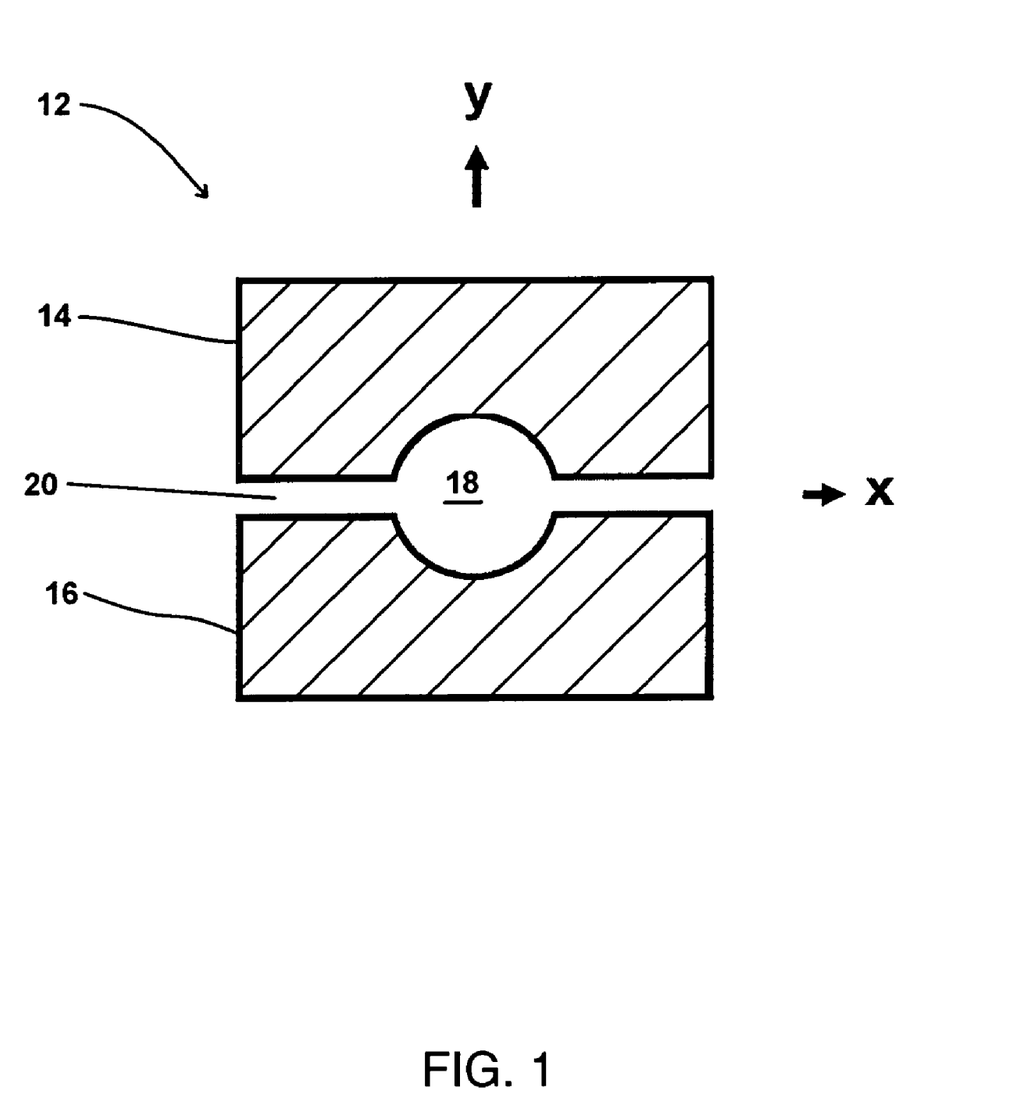
FIG. 1 is a cross section of an electrode assembly suitable for the present invention in which gap spacing is exaggerated.

Solutions were aged for 2 to 5 weeks and exposed to a 6×10$^5$ V/m DC field for 10 minutes. Semi-cylindrical electrodes were constructed from a 5 cm×5 cm×5.5 cm block of brass, with the center drilled out so that the sample tubes would fit snugly, and then split in half and material removed to create a 5 mm gap, as shown in FIG. 1. FIG. 1 shows a cross section of a suitable electrode assembly 12 having two halves 14, 16, a drilled out center 18 for containing the sample tubes, and an electrode gap 20. The gap 20 spacing is exaggerated in the electrode assembly 12 shown in FIG. 1. All sharp edges were rounded in the actual electrodes. The electrodes are insulated and held firmly in position by Delrin plates, screwed together to make a covered box, with 5 mm thick spacers to hold the cylindrical electrodes at the proper spacing. There are two long narrow gaps in the insulation, matching the electrode gap 20, so that most of the length of the sample tube is visible from either side, and there is a small hole in the bottom insulating plate, with a mount for an optical fiber. A Glassman EH regulated power supply provided 0-15 kV DC. At voltages higher than 8 kV, breakdown occurred near the rounded edges of the electrodes near the center 18 cylinder-gap 20 intersection, so experiments were limited to the range 7-8 kV.

Figure 2:
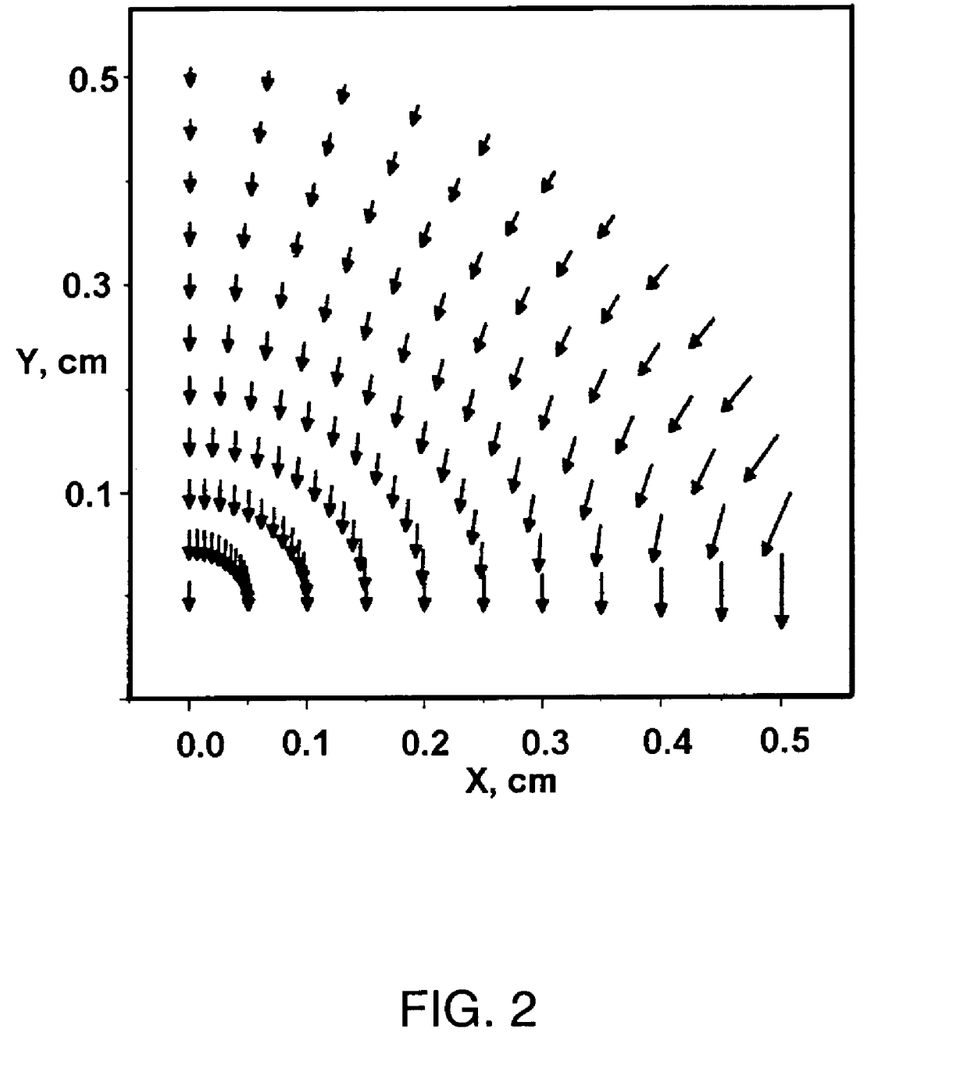
FIG. 2 is an electric field vector pattern for ideal infinite semi-cylindrical electrodes with a radius of 0.65 cm.

The electric field distribution in the region between the electrodes can be calculated assuming infinitely long semi-cylindrical electrodes. The resultant distribution is shown in FIG. 2. FIG. 2 is an electric field vector pattern for ideal infinite semi-cylindrical electrodes with a radius of 0.65 cm. Only one quadrant of the pattern is shown owing to the system symmetry. The electrode gap 20 is along the x-axis as shown in both FIGS. 1 and 2. If a unit potential of 1 V is applied to these electrodes, the magnitude of the resultant field ranges from 0.62 V/m near the inner tube wall on the y-axis to 2.4 V/m near the inner tube wall on the x-axis. For the main central area of the cross section, the resultant field is roughly constant, ranging from about 0.9 to 1.1 V/m. The actual field magnitude at a particular location in the solution is equal to these factors multiplied by the externally applied voltage, divided by the dielectric constant, ∈, of the solution, assumed to be equal to that of water ($\in_{water}$=80).

A low power monitoring continuous-wave laser beam at a wavelength of 532 nm, defocused in one direction with a cylindrical lens to generate a pencil-shaped beam, was directed through the electrode gap 20 and illuminated the length of the sample tube. The transmitted light was imaged on white paper. Light scattered perpendicular to the beam was collected with an optical fiber attached at the bottom of the cell and monitored with a power meter. The optical fiber and power meter were useful for monitoring the growth of slowly growing crystals over long time periods (hours), but imaging the transmitted beam on white paper was more useful for detecting the early stages of crystal growth. Small perturbations in the refractive index in the liquid, appearing as shadowy ripples in the imaged light, were often observed, even when crystals were too small to be seen with the naked eye, and before changes in the monitored power through the optical fiber indicated increased scattering due to crystal growth.

Crystals formed in the test tubes were removed from the solution and dried. The structure of these crystals was analyzed by grinding up the crystal into a powder and obtaining an x-ray powder diffraction pattern. The x-ray peaks obtained matched those of the γ polymorph of glycine. When the same analysis is carried out on control crystals formed when identical solutions are allowed to spontaneously nucleate, only the a polymorph is observed, thus supporting the premise of this invention.

Exposure to the DC field successfully induced the nucleation of γ glycine (33% at 1.9-2.0 SS after 14 days; 40% at 1.9-2.0 SS after 36 days; 24% at 1.85 SS after 16 days). These percentages represent the percent of the exposed solutions that nucleated within the 10-minute exposure time. Spontaneous nucleation rates at these concentrations for a ten-minute time window are 2 to 3 orders of magnitude lower (0.07% to 0.15% at 1.9-2.0 SS; 0.02% at 1.85 SS), so there is no doubt that nucleation was induced by the field. The fact that γ glycine was formed might at first seem like additional proof that the glycine was not spontaneously produced; however, we have found that at supersaturations above 1.8, the spontaneous nucleation of aged glycine solutions tend to produce a mixture of α and γ rather than the pure a polymorph that is produced spontaneously at lower supersaturations, with more γ the higher the concentration, as shown in Table 1. Towler et al. obtained a glycine up to an SS of 2.4, although their nucleation experiments are performed under agitation, whereas ours are carried out under quiescent conditions. Towler, C. S. et al., Journal of the American Chemical Society, Vol. 126, pp. 13347-13353 (2004). Aging appears to be critical to the polymorph obtained at high supersaturation. High concentration samples nucleated by agitation without aging produced the α polymorph. After even one day of aging, the dominant a polymorph showed "contamination" with the γ form.

Examination of Table 1 shows that DC-field induced nucleation shifts the polymorph distribution toward the γ polymorph and away from the α polymorph, compared to the distribution obtained by spontaneous nucleation. Given that γ glycine has a polar crystal structure, with all glycine dipoles pointing the same direction, whereas α glycine has a centrosymmetric structure, one would expect a DC field to preferentially induce the nucleation of the γ polymorph if electric-field induced orientation were occurring.

TABLE 1

Polymorphs obtained from aged aqueous glycine solutions under different nucleation conditions.

| SS | Nucleation conditions | Sample size | % samples pure α | % samples pure γ | % samples mixed α + γ |
|---|---|---|---|---|---|
| 1.85 | Spontaneous | 22 | 86 | 14 | 0 |
| 1.85 | DC field | 4 | 50 | 50 | 0 |
| 1.9–2.0 | Spontaneous | 15 | 13 | 60 | 27 |
| 1.9–2.0 | DC field | 5 | 0 | 100 | 0 |

Figure 3:
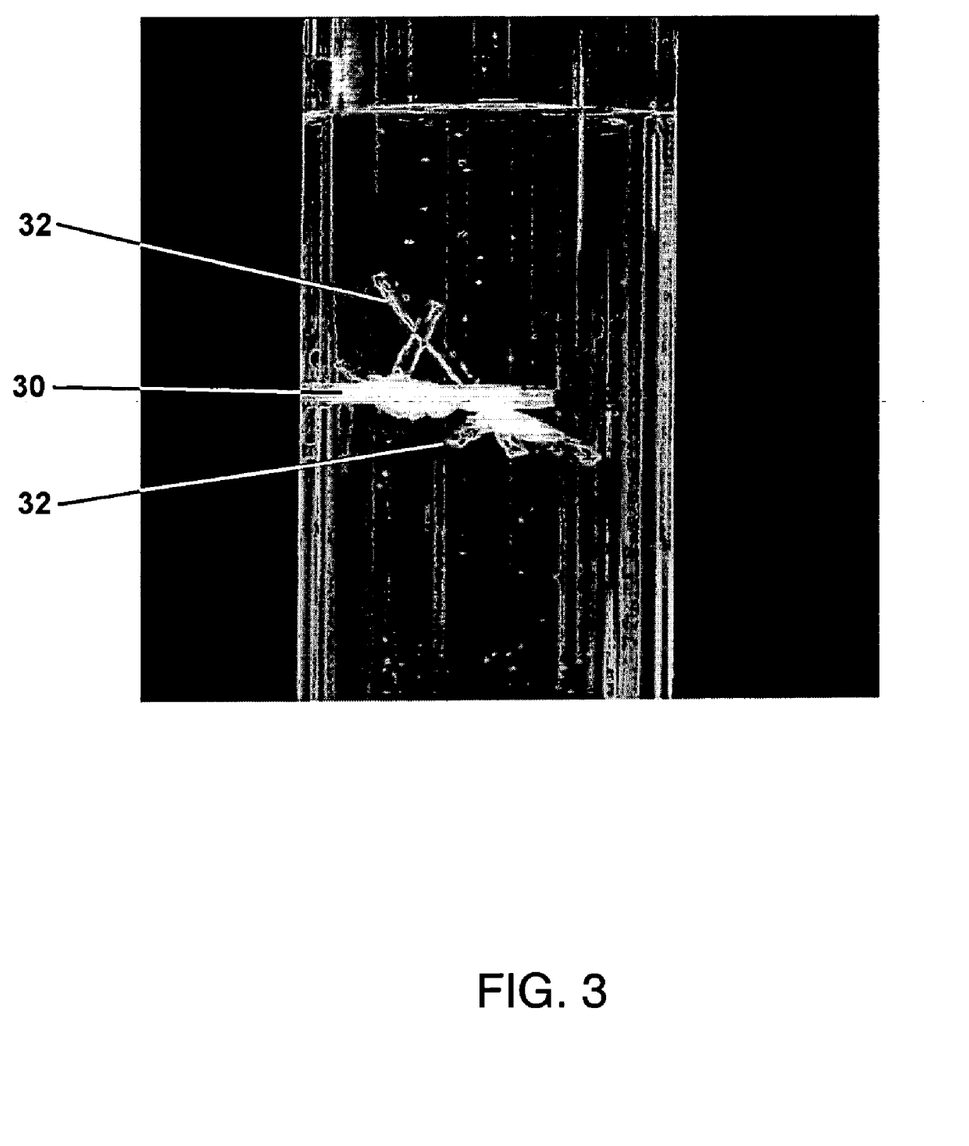
FIG. 3 is a photomicrograph that illustrates γ-glycine crystals formed with DC-electric field in induced nucleation using the process of the present invention.

The γ glycine crystals produced at high SS also exhibit a different morphology; they form needle-shaped crystals as shown in FIG. 3, and these needles grow faster than the pyramidal γ crystals formed at lower concentrations. The transparent needles 32 coming off the main horizontal mass 30 at an angle are the result of secondary nucleation. The fact that the initially formed needle 30 was oriented horizontally is consistent with its induction by the applied DC field, although the location of the initially observed crystal is independent of position in the sample tube relative to the electrodes. The needle morphology is also observed in spontaneously nucleating solutions at these high concentrations.

The aqueous glycine solutions that were exposed to DC fields have a pH of 6.4-6.5, which is close to, but not exactly at the isoelectric point of glycine (where the average charge on a glycine molecule is zero), which occurs at a pH of 6.0. At pH far from this value, there can be a substantial concentration of charged glycine species such as $^+NH_3CH_2COOH$ or $NH_2CH_2COO^-$. Such species, when subjected to a DC electric field, will tend to migrate toward the electrode with the opposite charge, effectively increasing the supersaturation near the electrode, which in itself can be responsible for inducing nucleation. Our calculations, based on the multiple equilibria among $^+NH_3CH_2COOH$, $NH_2CH_2COO^-$, $^+NH_3CH_2COO^-$ and $NH_2CH_2COOH$, indicate that for 5.7 molal glycine in pure water, ≧99.93% of the species present in solution are neutral zwitterions (compared with 99.96% at the isoelectric point), and thus the ion migration mechanism described above can be ruled out. Moreover, the pH of solutions made from neutral glycine are predicted to be largely insensitive to concentration.

Another potential cause of solute migration is electrostriction, in which polarizable molecules can minimize their energy by moving to regions of highest electric field. Because the electric field distribution in our sample tubes is not uniform, there are electrostrictive energy differences at different locations given by $\frac{1}{2}<\alpha>\Delta(E^2)$, where $<\alpha>$ is the average polarizability of glycine ($7\times10^{-40}$ C m$^2$/V) and $\Delta(E^2)=E_{max}^2-E_{min}^2=2\times10^{12}$ V$^2$/m$^2$. This gives a maximum energy difference of $10^{-7}$ kT, which is totally negligible.

We believe these DC-field induced experiments lend further support to our proposed optical-Kerr mechanism for NPLIN. Furthermore, it represents a new method for controlling nucleation in supersaturated solutions, and may provide another technique for controlling polymorph formation, and possibly forming new polymorphs.

The above description sets forth the best mode of the invention as known to the inventors at this time, and is for illustrative purposes only, as it is obvious to one skilled in the art to make modifications to this process without departing from the spirit and scope of the invention and its equivalents as set forth in the appended claims. The use of glycine for the experimental portion of this specification is for illustrative purposes only, as it is clear to one of ordinary skill in the art that the procedure and results disclosed and claimed in this specification can be performed for other compounds with polymorphs without undue experimentation.

What is claimed is:

1. A method of nucleating a crystal structure of a substance selected from the group consisting of amino acids, peptides, proteins, carbohydrates, amines, alkanes, alkenes, alkynes, aromatics, heterocyclic compounds, alcohols, organometallics, and carboxylic acids, the method comprising:
   preparing a supersaturated solution of the substance in a solvent;
   selecting an intensity of a static electric field necessary to prepare the crystal structure of the substance, wherein the static electric field is greater than 400,000 V/m but less than 800,000 V/m; and
   subjecting the supersaturated solution to the static electric field for a period of time of between 0.1 second and 10 hours to induce nucleation of the crystal structure of the substance, wherein the supersaturated solution is not affected chemically by the subjecting of the supersaturated solution to the static electric field.

2. The method of claim 1, wherein the supersaturated solution is subjected to the static electric field until at least a portion of the substance has crystallized.

3. The method of claim 2, wherein said preparing is achieved by a method selected from the group consisting of cooling, heating, solvent evaporation, and altering solvent composition, and wherein the solvent is selected from the group consisting of organic solvents, inorganic solvents, and supercritical solvents.

4. The method of claim 3, wherein the solvent is water.

5. The method of claim 3, wherein the substance is selected from the group consisting of amino acids, peptides, and proteins.

6. The method of claim 1, wherein the crystal structure obtained is different than a crystal structure that would spontaneously nucleate in the absence of the method.

7. The method of claim 1, wherein the crystal structure of the substance is different than the crystal structure that nucleates from the supersaturated solution under the same conditions when the selected static electric field is not present.

8. A method of forming crystals of a substance selected from the group consisting of amino acids, peptides, proteins, carbohydrates, amines, alkanes, alkenes, alkynes, aromatics, heterocyclic compounds, alcohols, organometallics, and carboxylic acids, the method comprising:
   preparing a supersaturated solution of the substance in a solvent;
   selecting an intensity of the static electric field necessary to prepare the crystals of the substance, wherein the static electric field is greater than 400,000 V/m but less than 800,000 V/m; and
   subjecting the supersaturated solution to the static electric field for a period of time of between 0.1 second and 10 hours to induce nucleation of the crystal form of the substance;

wherein the supersaturated solution is not affected chemically by said subjecting the supersaturated solution to the static electric field, and wherein the resulting crystal form is different than the expected or known resulting crystal form that would nucleate in the absence of the static electric field selected.

9. The method of claim 8, wherein the supersaturated solution is subjected to the static electric field until at least a portion of the substance has crystallized.

10. The method of claim 9, wherein said preparing is achieved by a method selected from the group consisting of cooling, heating, solvent evaporation, and altering solvent composition, and wherein the solvent is selected from the group consisting of organic solvents, inorganic solvents, and supercritical solvents.

11. The method of claim 10, wherein the solvent is water.

12. The method of claim 10, wherein the substance is selected from the group consisting of amino acids, peptides, and proteins.

13. The method of claim 8, wherein the crystal structure of the substance obtained is different than a crystal structure of the substance that would spontaneously nucleate in the absence of the method.

14. The method of claim 10, wherein the crystal structure of the substance that is different than the crystal structure that nucleates from the supersaturated solution under the same general conditions when the selected static electric field is not present.

* * * * *

UNITED STATES PATENT AND TRADEMARK OFFICE
CERTIFICATE OF CORRECTION

| | |
|---|---|
| PATENT NO. | : 7,879,115 B2 |
| APPLICATION NO. | : 11/104714 |
| DATED | : February 1, 2011 |
| INVENTOR(S) | : Garetz et al. |

It is certified that error appears in the above-identified patent and that said Letters Patent is hereby corrected as shown below:

Title page, item (56), under "Other Publications", in Column 2, Line 7, delete "Soluations?" and insert -- Solutions? --.

Column 1, Line 9, delete "2004, currently pending." and insert -- 2004. --.

Signed and Sealed this

Thirty-first Day of May, 2011

David J. Kappos
*Director of the United States Patent and Trademark Office*